United States Patent [19]

Matsuda

[11] 3,996,164

[45] Dec. 7, 1976

[54] CATALYSTS FOR HYDROFORMYLATION AND HYDROESTERIFICATION AND METHOD FOR MANUFACTURE THEREOF

[75] Inventor: Akio Matsuda, Kashiwa, Japan

[73] Assignee: Agency of Industrial Science & Technology, Tokyo, Japan

[22] Filed: June 20, 1975

[21] Appl. No.: 588,874

Related U.S. Application Data

[63] Continuation-in-part of Ser. No. 418,107, Nov. 21, 1973, abandoned.

[30] Foreign Application Priority Data

Nov. 25, 1972 Japan .............................. 47-118235

[52] U.S. Cl. ...................... 252/431 N; 260/270 E; 260/604 HF; 260/410.9 R; 260/270 J
[51] Int. Cl.² ...................... B01J 31/18; B01J 31/20
[58] Field of Search ............. 252/431 N; 260/270 J, 260/270 E

[56] References Cited

UNITED STATES PATENTS 3,636,159  1/1972  Solomon ..................... 252/431 N X
3,652,676  3/1972  Kahle et al. ................ 252/431 N X

OTHER PUBLICATIONS

Moffat, "New Oxo Chemistry Via Solid Polymer–Cobalt Carbonyl Complexes", J. Catalysis, 18, pp. 193–199 (1970).

Primary Examiner—Patrick P. Garvin
Attorney, Agent, or Firm—Kurt Kelman

[57] ABSTRACT

A complex formed by combining cobalt carbonyl with one member selected from the group consisting of pyridine, alkylpyridine and formylalkylpyridine makes a catalyst exceptionally suitable for both hydroformylation and hydroesterification of olefins, whereas a complex formed by combining cobalt carbonyl, pyridine and ketone makes a catalyst exceptionally suitable for hydroesterification of olefins.

The conditions required for the manufacture of this catalyst are included in the conditions for hydroformylation or those for hydroesterification. The formation of this catalyst and the hydroformylation or hydroesterification involving the use of said catalyst can be carried out continuously in a cyclic pattern.

7 Claims, No Drawings

CATALYSTS FOR HYDROFORMYLATION AND HYDROESTERIFICATION AND METHOD FOR MANUFACTURE THEREOF

REFERENCE TO COPENDING APPLICATION

This is a continuation-in-part application of my copending application U.S. Ser. No. 418,107 filed Nov. 21, 1973 now abandoned.

BACKGROUND OF THE INVENTION

This invention relates to novel catalysts for hydroformylation and hydroesterification of olefins, to a method for the manufacture of these novel catalysts, and to hydroformylation and hydroesterification of olefins by use of said catalysts.

Of the catalysts suggested to date for use in hydroformylation (oxo reaction) of olefins, those of particular importance are cobalt carbonyl, rhodium carbonyl and derivatives thereof. Those substances which give rise to such compounds in the reaction system may be similarly be used. Since hydroformylation is a reaction which is carried out in a liquid phase having the catalyst uniformly dissolved therein, separation of the catalyst from the hydroformylation product calls for a special measure. Particularly when the hydroformylation is carried out by using a cobalt type ctalyst, the separation of cobalt carbonyl from the resultant product has been a very important problem from the industrial point of view. In this connection numerous patents including U.S. Pat. No. 3,636,159 and 3,652,676 have issued to date. Actually, however, the separation of cobalt carbonyl has heretofore been performed preponderantly by following the methods to be described herein below: One method comprises heating the reaction product to have cobalt carbonyl thermally decomposed and subsequently educing the cobalt in the form of metallic cobalt. The other method comprises treating the reaction product with an organic acid or inorganic acid to have cobalt carbonyl converted into an oil-soluble, water-soluble or water-insoluble cobalt salt and subsequently separating the cobalt salt by such means as distillation or extraction, depending on the behavior of said cobalt salt or educing it in a solid form. The metallic cobalt or cobalt salt separated by these methods is converted again to cobalt carbonyl in a separate stage of process and put to use as the catalyst for the next cycle of oxo reaction. Otherwise, the metallic cobalt or cobalt salt may be recycled to the reaction system in its unaltered form. In this case, the interior of the oxo reaction vessel is required to be placed under conditions which permit conversion of the metallic cobalt or cobalt salt into cobalt carbonyl. The conditions involved herein are elevated temperature and increased pressure such as, for example, 150° – 200° C and 200 – 300 atmospheres. Another method available for the recovery of cobalt carbonyl comporises the steps of converting cobalt carbonyl into water-soluble $NaCo(CO)_4$ by using $Na_2CO_3$, separating the conversion product in the form of aqueous solution and having the separated aqueous solution reacted upon by sulfuric acid to produce $HCO(CO)_4$, which is recycled to serve as the catalyst in the oxo reaction system. Recently, a method for separating cobalt carbonyl by the steps of treating the reaction product with a high molecular coordinating agent for thereby converting cobalt carbonyl into a insoluble solid and subsequently separating the solid from the system has been under study. The conventional methods described above invariably call for special stages of treatment designed exclusively for the recovery of the catalyst in question. It is also known that a complex of cobalt carbonyl comprising a substituted pyridine with electronegative non-hydrocarbon group is a catalyst good for the oxo reaction (see U.S. Pat. No. 3,231,621). However, the catalyst removal in this case requires a special measure. In the case of the catalyst for hydroesterification, the method of U.S. Pat. No. 3,507,891 has been known. This method also requires use of special means for the separation and reuse of the catalyst.

A primary object of this invention is to provide novel catalysts for use in hydroformylation and hydroesterification of olefins which are active at an extraordinarily low temperature and under an extraordinarily low pressure, and which can be separated with extreme ease.

Another aobject of this invention is to provide a method for the manufacture of complexes which are novel catalysts for use in the hydroformylation and hydroesterification of olefins.

Still another object of this invention is to provide a method for the hydroformylation and hydroesterification of olefins by the use of said novel catalysts.

SUMMARY OF THE INVENTION

Cobalt carbonyl and one or more members selected from the group consisting of pyridine, alkylpyridine, formylalkylpyridine, and vinylpyridine are dissolved in a hydrocarbon or some other suitable solvent. The reactants are allowed to undergo reaction under conditions for hydroformylation or hydroesterification and the resultant reaction product is cooled. Otherwise, cobalt carbonyl, pyridine and one member selected from the group consisting of saturated ketones and unsaturated ketones are dissolved in a hydrocarbon or some other suitable solvent. The reactants are allowed to react at between normal room temperature and 110° C and under 1 – 20 atm. Consequently, a viscous phase or a solid phase separates from the solvent phase. This separated phase is substantially composed of a complex and makes a catalyst suitable for hydroformylation or hydroesterification of olefins. This complex is a novel substance the structure of which has been essentially established as by infrared absorption spectrum.

When an olefin is subjected to hydroformylation or hydroesterification using the complex as the catalyst, the resultant reaction mixture on cooling separates itself virtually completely into a phase composed of the complex and another phase containing the reaction product. The separated phase composed of the complex is such that the raw material olefin may be mixed therewith and then subjected to hydroformylation or hydroesterification.

This means that said reaction can be carried out repeatedly by using one and the same catalyst.

The catalyst can be recovered substantially completely. By using this catalyst in the hydroformylation or hydroesterification of a given olefin, a corresponding straight-chain ester or aldehyde can be produced selectively in high yields.

DETAILED DESCRIPTION OF THE INVENTION

The inventor pursued a concentrated study on the hydroesterification and hydroformylation of olefins by the use of catalysts composed of $Co_2(CO)_8$-pyridine derivatives. This study has led to a discovery that novel complexes are formed by the reaction of $Co_2(CO)_8$ with pyridine, alkylpyridine, formylalkylpyridine or vinylpyridine, or with pyridine and ketone, that these complexes exhibit catalytic activities for the hydroesterification and/or hydroformylation of olefins at an extraordinarily low temperature and pressure and that they are substantially soluble in hydrocarbon solvents under the reaction conditions of hydroesterification and/or hydroformylation but are substantially insoluble therein at normal room temperature and pressure. The present invention has been accomplished on the basis of this discovery.

First, a description will be made of the combination of $Co_2(CO)_8$-pyridine. A 300-ml vertical agitation type autoclave was charged with 20 millimol of $Co_2(CO)_8$, 80 millimol of pyridine and 100 ml of n-pentane as a hydrocarbon solvent and the reactants were allowed to undergo reaction under constant pressure (40 atm) of carbon monoxide containing one percent of hydrogen at 100° C for 2.5 hour. After the reaction, the autoclave was cooled to room temperature. Consequently, 11g of an orange-yellow crystalline complex separated from the n-pentane phase. This complex was tested for infrared absorption spectrum, assayed for Co content (%) of the complex and measured for count of CO's and $H_2$'s coordinated to each 1 gram atom of Co in the complex as described herein below. The Co content was determined by heating a fixed quantity of the complex together with 3N sulfuric acid to 100° C in a sealed glass vessel to convert Co present in the complex into an aqueous solution of Co ion and titrating the aqueous solution with EDTA. The count of CO and $H_2$ coordinated to each 1 gram of the complex was found by analyzing the gas evolved when a definite quantity of the complex was heated in a glass tube under nitrogen. Separately, the complex was subjected to elementary analysis with respect to C, H and N. Said crystalline solid was found to be a novel complex as described herein after. A study of the infrared absorption spectrum of this complex revealed a strong absorption band at 1890 cm$^{-1}$ characteristic of $Co(CO)_4^-$ (cobalt tetracarbonyl anion), and a small absorption at 2010 cm$^{-1}$ indicating the presence of another coordinated carbon monoxide. The analyses of the complex agreed with the composition, $H_2Co_3(CO)_9(Py)_5$ as shown in Table 1.

Table 1.

| | Co(%) | C(%) | H(%) | N(%) | Analysis of the complex Coordinated CO and $H_2$ | |
|---|---|---|---|---|---|---|
| | | | | | CO, | $H_2$(mmol/g) |
| Found | 20.8 | 48.6 | 3.25 | 8.50 | 10.5 | 1.10 |
| Calcd. as $H_2Co_3(CO)_9(Py)_5$ | 21.4 | 49.2 | 3.27 | 8.47 | 10.9 | 1.21 |

Therefore the complex has the structure of an ion pair consisting of an anion $Co(CO)_4^-$, and a cationic part which comprises Co, CO, Py (pyridine), and $H^+$. The estimated structure is:

$\{Co(H^+)_2(Py)_5(CO)\}\{Co(CO)_4^-\}_2$

In manufacturing a complex according to this invention from pyridine and $Co_2(CO)_8$, the molar ratio of cobalt carbonyl and pyridine should be in the range of 1 : (2 – 2.5 ), and the reaction should be carried out at a temperature in the range of from 80° to 160° C under a CO pressure in the range of from 4 to 200 kg/cm². The separation of this complex from the reaction mixture can be accomplished by cooling the mixture to below 30° C and discharging the gas remaining in the autoclave. The separated complex is a dark red viscous liquid because it contains a small proportion of impurities. In a completely refined form, the complex is a crystalline solid as has been stated above.

Now, a description will be made of the complex derived from $Co_2(CO)_8$ vinylpyridine. A 300-ml vertical agitation type autoclave was charged with 4 millimol of $Co_2(CO)_8$, 40 millimol of 2-vinyl pyridine and 30g of benzene as a hydrocarbon solvent and the reactants were allowed to undergo reaction under pressure of a mixed gas containing of hydrogen and carbon monoxide at a molar ratio of 1 : 1 at 140° C for 0.5 hour. During the reaction, the pressure of the autoclave interior decreased from the initial level of 131.5 atm. to 126 atm. After the reaction, the autoclave was cooled to below 30° C. Consequently, a dark red viscous phase separated from the benzene phase and settled below said benzene phase. When this viscous phase was joined with 100cc of added petroleum ether, placed under 50 atm. of pressure with carbon monoxide and agitated at 100° C, a reddish brown solid complex separated from the mixture on cooling of the autoclave. This complex was dried under vacuum and then tested for infrared absorption spectrum, assayed for Co content (%) of the complex and measured for count of CO's coordinated to each 1 gram atom of Co in the complex as described herein below. The Co content was determined by heating a fixed quantity of the complex in 3N sulfuric acid to 100° C to convert Co present in the complex into a aqueous solution of Co ion and titrating the aqueous solution with EDTA chelate. The count of CO coordinated to each 1 gram atom of Co was found by determining CO which was simultaneously produced. Separately, the complex was subjected to elementary analysis with respect to C, H and N. Said solid was found to be a novel complex as described herein after. A study of the infrared absorption spectrum of this complex revealed a strong absorption band each at 2000 cm$^{-1}$, 1880 cm$^{-1}$ and 1660 cm$^{-1}$. The absorption at 1880 cm$^{-1}$ was evidently due to the presence of $Co(CO)_4^-$ (cobalt tetracarbonyl anion), indicating that the complex was of an ion-paired structure $\{Co(CO)_n\}^+\{Co(CO)_4\}^-$. The absorption at 2000 cm$^{-1}$ was due to the presence of the cation moiety $\{Co(CO)_n\}^+$. The absorption at 1660 cm$^{-1}$ indicates the presence of N-formyl piperidine ring. It was gas chromatographically confirmed that the complex does not contain unaltered vinyl-pyridine, but that the complex contains a small portion of ethylpyridine as ligands. The count of CO coordinated to each gram atom of Co was found to be 2 – 2.5. The elementary analysis was 13 – 16% of Co, 55 – 59% of C, 4 – 5% of H, 6.9 – 7.6% of N and the balance to make up 100% of $O_2$ respectively by weight. This complex according to the present invention, therefore, is estimated to have the following structure by analogy with the above mentioned pyridine complex: $\{Co(H^+)(L)_4(CO)\}Co(CO)_4^-$, where, L is formylethylpyridine ($C_8H_9NO$), ethylpyridine ($C_7H_9N$), formylethyl-N-formylpiperidine ($C_9H_{15}NO_2$), or a mixture of these three ligands. The analytical result is compared with the calculated values as structure A, $HCo_2(CO)_5(C_8H_9NO)_4$, structure B, $HCo_2(CO)_5(C_8H_9NO)_3(C_7H_9N)$, and structure C, $HCo_2(CO)_5(C_8H_9NO)_3(C_9H_{15}NO_2)$.

Table 2.

Comparison of analytical result with calculated values.

|  |  | Co(%) | C(%) | H(%) | N(%) |
|---|---|---|---|---|---|
| Found |  | 13–16 | 55–59 | 4–5 | 6.9–7.6 |
| Calcd. as structures | A | 14.77 | 55.27 | 4.63 | 7.01 |
|  | B | 15.30 | 56.03 | 4.80 | 7.26 |
|  | C | 14.17 | 54.74 | 5.16 | 6.72 |

Accordingly, the complex of the present invention is mainly composed of a compound of formula A, $HCo_2(CO)_5(C_8H_9NO)_4$, and compounds of formulas B and C, in which one of for $C_8H_9NO$ ligands is replaced by $C_7H_9N$ or $C_9H_{15}NO_2$ may be contained in the complex as impurities.

As mentioned above, the complex formed by combining $Co_2(CO)_8$ with vinylpyridine does not contain nonreacted vinyl-pyridine but formylethylpyridine ($C_8H_9NO$), ethylpyridine ($C_7H_9N$) and formylethyl-N-formylpiperidine ($C_9H_{15}NO_2$) as ligands.

That is to say, a complex identical with said complex ought to be also obtained by reacting $Co_2(CO)_8$ with formylethylpyridine, ethylpyridine and formylethyl-N-formylpiperidine (without using vinylpyridine).

In manufacturing a complex according to this invention from vinyl pyridine and $Co_2(CO)_8$, the ratio of cobalt carbonyl, vinyl pyridine and a hydrocarbon as the solvent should be in the range of 1 : (1 ~ 10) : (4 ~ 30) by weight and the reaction should be carried out at a temperature in the range of from 80° C to 200° C under a CO pressure in the range of from 10 kg/cm² to 200 kg/cm². The separation of this complex from the reaction mixture can be accomplished by cooling the mixture to below 30° C. In the aforementioned method of manufacture, the complex is separated from the mixture by cooling the mixture to below 30° C. Since this occurs as a mere phase separation, the separated complex is a dark red viscous liquid because it contains a small proportion of impurities. In a completely refined form, the complex is solid at temperatures below 30° C.

It has been ascertained that the complex is substantially soluble in hydrocarbon solvents under the reaction conditions of not less than 80° C and 10 atm. of carbon monoxide pressure, and substantially insoluble in said solvents at temperatures not more than 30° C and that it occurs as a reddish brown solid at temperatures not more than 30° C.

For the manufacture of the complex mentioned above, both 2-vinyl pyridine and 4-vinyl pyridine can be used. Use of 4-vinyl pyridine, however, is more desirable for the manufacture of the catalyst for hydroesterification. For the catalyst to be used in producing with advantageous selectivity a straightchain aldehyde by hydroformylation of an olefin, 2-vinyl pyridine is more desirable.

Now, the combination of $Co_2(CO)_8$, pyridine and ketone will be described.

To a solution of 4 mmol of $Co_2(CO)_8$ in 50 ml of n-pentane were added 16 mmol of pyridine and 17 mmol of acetone, and the mixture was allowed to react at normal room temperature and under the normal atmospheric pressure of carbon monoxide. On standing for about 10 hours, red-brown crystalline solid separated from the n-pentane phase. Then this complex was tested for infrared absorption spectrum, assayed for Co content (%) of the complex and measured for moles of coordinated carbon monoxide per each 1 gram of the complex as described herein below. The Co content was determined by heating a fixed quantity of the complex in 3N sulfuric acid to 100° C to convert Co present in the complex into an aqueous solution of Co ion and titrating the aqueous solution with EDTA. The count of CO coordinated to each 1 gram of the complex was found by analyzing the gas evolved when a definite quantity of the complex was heated in a glass tube under nitrogen. Separately, the complex was subjected to elementary analysis with respect to C, H, and N. In the infrared absorption spectrum, a strong absorption band was observed at 1890 cm⁻¹. This evidently indicates that the complex contains a cobalt carbonyl anion represented by $Co(CO)_4^-$. The spectrum also showed a band at 2010 cm⁻¹ and a band at 1710 cm⁻¹. The band at 2010 cm⁻¹ indicates the presence of coordinated carbon monoxide other than the above-mentioned $Co(CO)_4^-$, and the band at 1710 cm⁻¹ indicates the presence of coordinated acetone. Analytical results agreed with the composition, $Co_5(CO)_{13}(C_5H_5N)_n(C_3H_6O)_2$, where n=8 or 9.

Table 3.

Comparison of the analytical results with calculated values as $Co_5(CO)_{13}(C_5H_5N)_n(C_3H_6O)_2$

|  |  | Co(%) | C(%) | H(%) | N(%) | Coordinated CO (mmol/g) |
|---|---|---|---|---|---|---|
| Found |  | 19.4 | 49.0 | 3.65 | 8.18 | 8.87 |
| Calcd. | n=8 | 20.97 | 50.32 | 3.70 | 7.96 | 9.42 |
|  | n=9 | 19.85 | 51.68 | 3.84 | 9.48 | 8.75 |

This complex according to the present invention, therefore, is estimated to have the following structure: $\{Co_2(C_5H_5N)_n(C_3H_6O)_2(CO)\}^{+++}\{Co(CO)_4^-\}_3$ where, n is 8 or 9.

In manufacturing a complex according to this invention from $Co_2(CO)_8$, pyridine and acetone, the molar ratio of cobalt carbonyl, pyridine and acetone in a hydrocarbon solvent should be in the range of 1 : (4 – 5) : (1 – 10), and the mixture is allowed to react at a temperature preferably in the range of from normal room temperature to 110° C under the carbon monoxide pressure preferably in the range of from 1 to 20 atm.

As mentioned above, the catalyst of the present invention can be produced by combining cobalt carbonyl with at least one member selected from the group consisting of pyridine, alkylpyridine, formylalkylpyridine and vinylpyridine. However, when vinylpyridine is used as the raw material, the catalyst produced contains no vinylpyridine therein, because the vinyl radical is changed to alkyl radical during the catalyst manufacturing process.

Now, the hydroformylation and hydroesterification of olefins by the use of the catalysts of this invention will be explained herein below.

The catalysts of the present invention are manufactured by the methods already described. The conditions for this manufacture are included in the conditions which are required to be satisfied for the hydroformylation and hydroesterification of olefins. This means that the formation of the catalyst and the hydroformylation or hydroesterification can be carried out the hydroformylation or hydroesterification can be carried out continuously in a cyclic manner.

The complex formed to serve as the catalyst has a characteristic property such that it remains in a dissolved state in the hydrocarbon solvent at elevated temperatures and is insolubilized and completely separated out of the solvent as the temperature is lowered below a stated level. When a hydrocarbon solvent containing a given olefin is added to a complex manufactured to be used as the catalyst by one of the aforementioned methods, the complex forms a separate phase from the solvent phase so far as the mixture is kept at normal room temperature. Once this mixture is heated to temperatures (80° – 160° C) for the purpose of hydroformylation of hydroesterification, the complex uniformly dissolves in the hydrocarbon solvent containing the olefin. The reactants in the mixture are caused to undergo reaction as the mixture is subjected to pressure of carbon monoxide or a mixture of carbon monoxide and hydrogen. When the reaction solution is cooled after termination of the reaction, the complex is again separated in the form of a dark red viscous liquid from the solvent containing the reaction product. The separated complex is once again joined with a fresh supply of raw material and a solvent to repeat the reaction. The complex thus separated from the reaction product is as active in the next cycle of reaction as it was in the first cycle. In cyclic use of the catalyst, therefore, there is absolutely no necessity for such additional stage of operation as that for activation. After termination of the reaction, a very small fraction (1 – 10%) of the cobalt originally present in the catalyst dissolves into the solvent containing the reaction product. The cobalt thus dissolved into the solvent can be recovered in the form of a distillation residue when the reaction product and the solvent are subjected to distillation under reduced pressure. The distillation residue containing the recovered cobalt may be added to said complex and recycled to the reactiion system for reuse. This means that the catalyst can be recovered theoretically by 100%.

The catalysts of this invention differ from the conventional catalysts. For example, the catalysts are formed when the raw materials are treated under conditions for hydroformylation and hydroesterification. The catalyst thus formed can be obtained without requiring any special means of separation. When an olefin and a hydrocarbon solvent are added to the formed catalyst and the resultant mixture is subjected to hydroformylation or hydroesterification under required conditions, the product aimed at can be obtained in exceptionally high yields. The catalyst in the reaction solution can easily be recovered by merely cooling the reaction solution. The recovered catalyst can be used for the subsequent cycle of hydroformylation or hydroesterification. The catalyst retains its activity intact. Theoretically, the catalyst can be recovered by 100%.

The catalysts of this invention are more active at conspicuously lower temperatures and pressure than the conventional catalysts. Compared with the conventional oxo reaction catalyst, $Co_2(CO)_8$, which is effective under reactions of 130° to 200° C and 100 to 300 atm., the catalysts of this invention provide the desired catalytic activity at much lower temperature and pressure and give a straight-chain product in high yields. Thus, it is suitable for commercial operations. For example, methyl undecanoate can be obtained in a yield of 69% when 1-decene, methanol and benzene as the solvent are added to the complex produced from $Co_2(CO)_8$ and 4-vinyl pyridine and the resultant mixture is subjected to hydroesterification at 100° C under 20 atm. of pressure of carbon monoxide.

Examples of the olefins which can be subjected to hydroformylation and hydroesterification using the catalysts of this invention include monoolefins such as decene and propylene and dienes such as butadiene.

Hydroformylation and hydroesterification carried out by the use of these catalysts produce straight-chain aldehydes and straight-chain esters in high yields.

The following examples are further illustrative of this invention and it should be understood that the present invention is not limited thereto.

EXAMPLE 1

A 300-ml stainless steel-made autoclave fitted with an agitator was charged with 10g (0.095 mol) of 4-vinyl pyridine, 3.2g (0.1 mol) of methanol, 70g of benzene and 10g (0.029 mol) of dicobalt octacarbonyl. Under pressure of carbon monoxide, the mixture was allowed to react at 180° C for 7 hours. During the reaction, the pressure inside the autoclave was in the range of from 145 to 131 atm. When the autoclave was cooled after termination of the reaction, the complex of cobalt carbonyl with the carbonylation product of 4-vinyl pyridine occurred in the form of a dark red viscous liquid settled to the autoclave bottom and formed a phase separately of an upper phase containing benzene. Then, hydroesterification of 1-decene was repeated by using said complex in the lower phase as a catalyst. To permit observation of the behavior of this catalyst during the reaction, said complex was moved into an autoclave made of pressure proof glass. Then a solution consisting of 0.1 mol of 1-decene, 0.1 mol of methanol and 30g of benzene was added to the catalyst. The autoclave was closed. The air in the interior of the autoclave was displaced with carbon monoxide and was compressed to 7 atm. At this point, benzene containing 1-decene and methanol formed a clear, colorless upper phase separately of the complex. As the autoclave was heated and the contents were simultaneously agitated, the dark red complex gradually dissolved into the upper phase. By the time the autoclave contents reached the reaction temperature of 90° C, the contents became a thoroughly uniform dark red solution and the absorption of gas in consequence of the progress of reaction was observed to start. The reaction was continued at 90° C under 10 atm. for 4 hours. At the end of the reaction, the autoclave was cooled to normal room temperature. Consequently, the complex again separated itself to form a dark red lower phase separately of a light orange upper phase containing the reaction product. The complex which had separated from the reaction product was transferred into said stainless steel-made autoclave, wherein 0.1 mol of 1-decene, 0.1 mol of methanol and 30g of benzene were added to the catalyst and subjected to the same reaction. When the autoclave was cooled after termination of the reaction, the complex again precipitated and formed a separate phase. The upper phase containing the reaction product was withdrawn and subjected to gas chromatographic analysis to find the conversion of 1-decene and the yields of reaction products based on the converted 1-decene. A part of the reaction product phase was joined with 3N sulfuric acid and heated to have the dissolved cobalt converted into aqueous solution of cobalt ion. The aqueous solution was subjected to chelate titration using EDTA by way of analysis for cobalt dissolved in the reaction product phase. Reaction conditions employed in different runs of the test and analyses obtained for these runs are shown in Table 4. Run Nos. indicate the sequence of successive runs of the test performed. In the table, the term "isomerized decene" represents the sum of decenes formed in consequence of the isomerization of 1-decene. $E_1$ stands for methyl undecanoate and $E_2$ for $\alpha$-methyl methyldecanoate. The term "dissolved cobalt" means the ratio of cobalt which was dissolved into the reaction product phase after termination of the reaction to cobalt which was present in the catalyst at the start of each run of test.

The analysis was conducted by the method described in Example 1. Reaction conditions used in different runs of the test and analyses obtained for these runs are shown in Table 5. Run Nos. indicate the sequence of the successive runs of the test performed. The symbols found in the table are the same as those of Table 4.

Table 5

| Run No. | Temperature (° C) | Pressure (atm) | Time (min) | Conversion (%) | Yield (%) based on converted 1-decene | | | | Dissolved Co (%) |
|---|---|---|---|---|---|---|---|---|---|
| | | | | | Isomerized decene | Decane | $E_1$ | $E_2$ | |
| 1 | 140 | 100 | 60 | 99 | 3.7 | 0.78 | 48 | 9.9 | 5.0 |
| 2 | 140 | 90 | 40 | 100 | 4.0 | 0.77 | 61 | 12 | 3.9 |
| 3 | 100 | 20 | 120 | 81 | 14 | 0.96 | 69 | 14 | 3.8 |
| 4 | 110 | 20 | 105 | 100 | 19 | 0.75 | 60 | 11 | 4.6 |
| 5 | 100 | 10 | 120 | 68 | 28 | 0.93 | 61 | 9.3 | 4.6 |

EXAMPLE 3

The same autoclave as used in Example 1 was charged with 4.2g (40 millimol) of 2-vinyl pyridine, 30g of benzene and 1.37g (4 millimol) of dicobalt octacarbonyl. By use of a mixed gas consisting of hydrogen and carbon monoxide at a molar ratio of 1 : 1, the mixture was allowed to undergo reaction at 140° C for 0.5 hour. During the reaction, the pressure inside the Table 4

| Run No. | Temperature (° C) | Pressure (atm) | Time (min) | Conversion (%) | Yield (%) based on converted 1-decene | | | | Dissolved Co (%) |
|---|---|---|---|---|---|---|---|---|---|
| | | | | | Isomerized decene | Decane | $E_1$ | $E_2$ | |
| 1* | 90 | 10 | 240 | 10 | — | — | 88 | 12 | 1.3 |
| 2 | 100 | 20 | 120 | 75 | & 21 | 2.1 | 51 | 6.3 | 4.2 |
| 3 | 100 | 40 | 120 | 73 | 6.6 | 1.7 | 62 | 11 | 3.6 |
| 4 | 100 | 60 | 120 | 52 | 2.7 | 2.7 | 63 | 11 | 4.9 |
| 5 | 100 | 30 | 120 | 79 | 12 | 1.8 | 67 | 12 | 4.0 |

*Autoclave made of pressure proof glass used

EXAMPLE 2

The same stainless steel-made autoclave as used in Example 1 was charged with 15g (0.14 mol) of 4-vinyl pyridine, 60g of benzene and 10g (0.029 mol) of dicobalt octacarbonyl. By use of a mixed gas consisting of hydrogen and carbon monoxide at a molar ratio of 1 : 1, the mixture was allowed to undergo reaction at 140° C for 0.5 hour. During the reaction, the pressure inside the autoclave was in the range of 110 – 94 atm. When the autoclave was cooled after termination of the reaction, the complex of cobalt carbonyl with 4-vinyl pyridine occurred in the form of a dark red viscous liquid and settled to form a lower phase separately of an upper phase containing benzene. Hydroesterification of 1-decene was repeated by using said complex as a catalyst. The reaction was carried out by having 0.1 mol of 1-decene, 0.25 mol of methanol and 30g of benzene added to the autoclave containing said complex and subjecting the mixture to reaction under pressure of carbon monoxide, with the reaction conditions varied from one run to another of the test. When the autoclave was cooled after termination of the reaction, the complex separated from the benzene phase containing the reaction product and settled to the bottom.

autoclave was in the range of 131.5 – 126 atm. When the autoclave was cooled after termination of the reaction, the complex of cobalt carbonyl with the carbonylation product of 2-vinyl pyridine settled in the form of a dark red viscous liquid to the bottom of the autoclave separately of an upper phase containing benzene. Then, hydroformylation of 1-decene was repeated by using said complex as a catalyst. The reaction was carried out by having 0.1 mol of 1-decene and 30g of benzene added to the autoclave containing said complex and causing the mixture to undergo reaction under pressure of a mixed gas consisting of hydrogen and carbon monoxide at a molar ratio of 1 : 1, with the reaction conditions varied from one run to another of the test. When the autoclave was cooled after termination of the reaction, the complex again settled to the bottom of the autoclave and formed a lower phase separately of a light orange upper phase containing the reaction product. The analysis was conducted by the same method as described in Example 1. Reaction conditions used in different runs of the test and analyses obtained for these runs are shown in Table 6. Run Nos. indicate the sequence of the successive runs of test performed. In the table, $A_1$ and $A_2$ stand for undecanal and $\alpha$-methylundecanal respectively. The other symbols are the same as those used in Table 4.

Table 6

| Run No. | Temperature (° C) | Pressure (atm) | Time (min) | Conversion (%) | Yield (%) based on converted 1-decene | | | | Dissolved Co (%) |
|---|---|---|---|---|---|---|---|---|---|
| | | | | | Isomerized decene | Decane | $A_1$ | $A_2$ | |
| 1 | 140 | 200 | 20 | 100 | 4.5 | 2.2 | 59 | 19 | 4.2 |
| 2 | 140 | 200 | 20 | 100 | 3.4 | 2.0 | 63 | 17 | 5.9 |
| 3 | 120 | 150 | 30 | 91 | 7.7 | 1.8 | 63 | 16 | 6.4 |
| 4 | 120 | 150 | 30 | 93 | 4.8 | 1.6 | 69 | 18 | 4.9 |

EXAMPLE 4

The same stainless steel-made autoclave as described in Example 1 was charged with 4.2g (40 millimol) of 2-vinyl pyridine, 0.16g (5 millimol) of methanol, 30g of benzene and 1.37g (4 millimol) of dicobalt octacarbonyl. Under pressure of carbon monoxide, the mixture was allowed to undergo reaction at 180° C for one hour. During the reaction, the pressure inside the autoclave was in the range of 150 – 148 atm. When the autoclave was cooled after termination of the reaction, the complex of cobalt carbonyl with the carbonylation product of 2-vinyl pyridine occurred in the form of a dark red viscous liquid, settled to the bottom of the autoclave and formed a lower phase separately of an upper phase containing benzene. Then, a reaction involving 0.1 mol of 1-decene and 30g of benzene and using said complex as a catalyst was performed under pressure of a mixed gas consisting of hydrogen and carbon monoxide at a molar ratio of 1 : 1, with reaction conditions varied from one run to another of the test. When the autoclave was cooled after termination of the reaction, the complex again settled to the bottom of the autoclave and formed a lower phase separately of an upper phase containing the reaction product. The analysis was carried out by the same method as described in Example 1. Reaction conditions used in different runs of the test and analyses obtained for these runs are shown in Table 7. Run Nos. indicate the sequence of successive runs of the test performed. The symbols found in the table are the same as those of Table 6.

nol, 30g of toluene and 1.37g (4 millimol) of dicobalt octacarbonyl. Under pressure of carbon monoxide, the mixture was allowed to undergo reaction at 180° C for one hour. During the reaction, the pressure inside the autoclave was in the range of 150 – 146 atm. When the autoclave was cooled after termination of the reaction, the complex of cobalt carbonyl with the carbonylation product of 2-vinyl pyridine occurred in the form of a dark red viscous liquid, settled to the bottom of the autoclave and formed a lower phase separately of an upper phase containing toluene. Then a reaction involving 0.1 mol of propylene and 30g of toluene and using said complex as a catalyst was carried out under pressure of a mixed gas consisting of hydrogen and carbon monoxide at a molar ratio of 1 : 1, with the reaction conditions varied from one run to another of the test. When the autoclave was cooled after termination of the reaction, the complex again settled to the bottom of the autoclave and formed a phase separately of the phase of the reaction product. The conversion of propylene and the yields of n-butylaldehyde and iso-butylaldehyde based on the converted propylene were determined by analysing the residual gas and the phase of the reaction product by gas chromatography. The cobalt which had dissolved into the phase of the reaction product was analyzed by the same method as described in Example 1. Reaction conditions used in different runs of the test and analyses obtained for these runs are shown in Table 8. Run Nos. indicate the sequence of successive runs of the test performed. In the table, n-B and i-B stand for n-butylaldehyde and iso- Table 7

| Run No. | Temperature (° C) | Pressure (atm) | Time (min) | Conversion (%) | Yield (%) based on converted 1-decene | | | | Dissolved Co (%) |
|---|---|---|---|---|---|---|---|---|---|
| | | | | | Isomerized decene | Decane | $A_1$ | $A_2$ | |
| 1 | 120 | 150 | 30 | 88 | 8.4 | 2.5 | 64 | 16 | 4.8 |
| 2 | 100 | 150 | 90 | 76 | 4.8 | 2.5 | 68 | 16 | 3.8 |
| 3 | 100 | 100 | 90 | 85 | 4.3 | 2.1 | 66 | 16 | 6.2 |
| 4 | 100 | 50 | 90 | 79 | 11 | 2.7 | 61 | 21 | 5.1 |

EXAMPLE 5

The same stainless steel-made autoclave was described in Example 1 was charged with 6.3g (60 millimol) of 2-vinyl pyridine, 0.24g (7.5 millimol) of methabutylaldehyde respectively. The other symbols are the same as those of Table 4.

Table 8

| Run No. | Temperature (° C) | Pressure (atm) | Time (min) | Conversion (%) | Yield (%) based on converted propylene | | Dissolved Co (%) |
|---|---|---|---|---|---|---|---|
| | | | | | n-B | i-B | |
| 1 | 100 | 150 | 4 | 62 | 70 | 19 | 1.9 |
| 2 | 140 | 150 | 0.5 | 98 | 69 | 26 | 1.6 |
| 3 | 120 | 150 | 2 | 98 | 76 | 21 | 0.5 |

EXAMPLE 6

The same stainless steel-made autoclave as described in Example 1 was charged with 31.5g (0.3 mol) of 4-vinyl pyridine, 60g of benzene and 10g (0.029 mol) of dicobalt octacarbonyl. By use of a mixed gas consisting of hydrogen and carbon monoxide at a molar ratio of 1 : 1, the mixture was allowed to undergo reaction at 140° C for two hours. During the reaction, the pressure inside the autoclave was in the range of 113 – 84 atm. When the autoclave was cooled after termination of the reaction, the complex of cobalt carbonyl with the carbonylation product of 4-vinyl pyridine occurred in the form of a dark red viscous liquid and formed a lower phase separately of an upper phase containing benzene. Then, hydroesterification of butadiene was repeated by using said complex as a catalyst. The reaction was carried out by having 0.1 mol of butadiene, 0.25 mol of methanol and 30g of benzene placed in said autoclave and subjecting the mixture to reaction under 200 atm. of pressure of carbon monoxide at 130° C for two hours. When the autoclave was cooled after termination of the reaction, the complex separated from an upper phase of benzene containing the reaction product. The conversion of butadiene and the yields of products based on the converted butadiene were determined by subjecting the residual gas and the upper phase containing the reaction product to gas chromatography. The test was repeated by using as a catalyst the complex settled to the bottom of the autoclave. The results are shown in Table 9. Run Nos. indicate the sequence of successive runs of the test performed. In the table, the results for Run No. 4 represent those obtained of a reaction carried out by using, as a catalyst, the cobalt portions (5.0g) which had dissolved into the reaction product phases of Run Nos. 1 through 3 and which were later recovered in the form of a distillation residue said reaction product phases and subjecting the combined phase to distillation under reduced pressure, in addition to the complex which had settled to the bottom of the autoclave at the end of Rub No. 3.

Table 9

| Run No. | Conversion of butadiene | Yield (%) based on converted butadiene | |
|---|---|---|---|
| | | Methyl-3-pentenate | 4-vinyl-1-cyclohexane |
| 1 | 81 | 91 | 8.9 |
| 2 | 80 | 74 | 11 |
| 3 | 80 | 73 | 14 |
| 4 | 82 | 84 | 9.3 |

EXAMPLE 7

The same stainless steel-made autoclave as described in Example 1 was charged with 40 millimol of 2-vinyl pyridine, 40 millimol of methanol, 30g of benzene and 4 millimol of dicobalt octacarbonyl. Under 155 atm. of pressure of carbon monoxide, the mixture was allowed to undergo reaction at 120° C for 30 minutes and further reaction at 200° C under 185 atm. of pressure for 2 hours. When the autoclave was cooled and the residual gas was purged after termination of the reaction, the complex of cobalt carbonyl with the hydroesterification product of 2-vinyl pyridine occurred in the form of a dark red viscous liquid and settled to form a lower phase separately from an upper phase containing benzene. Then, hydroformylation of 1-decene was carried out by using sad complex as a catalyst. This reaction was performed by having 0.1 mol of 1-decene and 30g of benzene added to the autoclave containing the complex and subjecting the mixture to reaction at 110° C for 20 minutes under pressure of a mixed gas consisting of hydrogen nand carbon monoxide at a molar ratio of 1 : 1. During the reaction, the pressure inside the autoclave was in the range of 98 – 85 atm. When the autoclave was cooled and the residual gas was purged after termination of the reaction, 90% of the original complex settled again in the form of dark red viscous liquid and separated from the benzene phase containing the reaction product. The settled complex was recovered. The reaction product was analyzed by gas chromatograph. It was consequently found the the conversion of 1-decene was 90%, the yields of reaction products based on the converted 1-decene were 69% of undecanal, 21% of α-methyldecanal and 2.3% of decane and the total of inner decenes formed in consequence of the isomerizaton of 1-decene was 6.4%.

EXAMPLE 8

The same stainless steel-made autoclave as described in Example 1 was charged with 32 millimol of 4-vinyl pyridine, 32 millimol of methanol, 30g of benzene and 10 millimol of dicobalt octacarbonyl. Under pressure of carbon monoxide, the mixture was allowed to undergo reaction first at 140° C under 170° atm. for 30 minutes and then at 200° C under 200 atm. for 2 hours. When the autoclave was cooled and the residual gas was purged after termination of the reaction, the complex of cobalt carbonyl with the hydroesterification product of 4-vinyl pyridine settled to form a lower phase in the form of a dark red viscous liquid separately of an upper phase containing benzene. Then, hydroesterification of 1-decene was carried out by using said complex of the lower phase as a catalyst. The reaction was performed by having 0.1 mol of 1-decene, 0.12 mol of methanol and 30g of benzene added to the autoclave containing said complex and subjecting the mixture to reaction under 50 atm. of pressure of carbon monoxide at 120° C for 30 minutes. When the autoclave was cooled and the residual gas was purged after termination of the reaction, 91% of the complex again settled in the form of a dark red precipitate and separated from the benzene phase containing the reaction product. The settled complex was recovered. The reaction product was analyzed by gas chromatography. Consequently, it was found that the conversion of 1-decene was 89% and the yields of reaction products based on the converted 1-decene were 65% of methyl undecanoate, 11% of α-methyl methyldecanoate and 2.0% of decane and the total of inner decenes formed in consequence of the isomerizaton of 1-decene was 18%.

EXAMPLE 9

The same stainless steel-made autoclave as described in Example 1 was charged with 40 millimol of 1,2-di-(4-pyridyl)-ethylene, 30g of benzene and 4 millimol of dicobalt octacarbonyl. Under 155 atm. of pressure of carbon monoxide containing 2% of hydrogen, the mixture was allowed to under reaction at 180° C for 30 minutes. When the autoclave was cooled to normal room temperature and the residual gas was purged after termination of the reaction, the complex of cobalt carbonyl with the carbonylation product of 1,2-di-(4-pyridyl)-ethylene educed in the form of an orange solid to the bottom of the autoclave. Then, hydroesterification of 1-decene was carried out by using the educed complex as a catalyst. The reaction was performed by having 0.1 mol of 1-decene, 0.12 mol of methanol and 30g of benzene added to the autoclave containing said complex and subjecting the mixture to reaction under pressure of carbon monoxide at 140° C for one hour. During the reaction, the pressure inside the autoclave was in the range of 143 – 136 atm. When the autoclave was cooled and the residual gas was purged after termination of the reaction, 99% of the complex again educed in the form of an orange solid to the bottom of the autoclave. This settled complex was recovered. The reaction product was analyzed by gas chromatography. Consequently, it was found that the conversion of 1-decene was 89%, the yields of reaction products based on the converted 1-decene were 54% of methyl undecanoate, 10% of α-methyl methyldecanoate and 2.0% of decane and the total of inner decenes formed in consequence of the isomerization of 1-decene was 14%.

EXAMPLE 10

There was placed in the same stainless steel-made autoclave as described in Example 1, a portion 1.5g (containing 3.2 mg. atom of Co), of the complex which was recovered during the procedure of Example 1, agitated in petroleum ether under 50 atm. of pressure of carbon monoxide at 100° C, cooled, recrystallized and dried under vacuum. Next was added 0.1 mol of 1-decene and 30g of benzene. The resulting mixture was subjected to hydroformylation at 120° for 20 minutes under pressure of a mixed gas consisting of hydrogen and carbon monoxide at a molar ratio of 1 : 1. During the reaction, the pressure inside the autoclave was in the range of 99 – 87 atm. When the autoclave was cooled and the residual gas was purged after termination of the reaction, 90% of the complex again settled in the form of an orange solid to the bottom of the autoclave. The settled complex was recovered. The reaction product was analyzed by gas chromatography. Consequently, it was found that the conversion of 1-decene was 89%, the yields of reaction products based on the converted 1-decene were 56% of undecanal, 21% of α-methyldecanal and 2.6% of decane and the total of inner decenes formed in consequence of the isomerization of 1-decene was 6.1%.

EXAMPLE 11

A 300-ml stainless steel-made vertical agitation type autoclave fitted with a pair of pressure-proof glass windows was charged with 14g (0.1 mol) of 1-decene, 4g (0.125 mol) of methanol, 30g of benzene, 3.42g (10 mmol) of $Co_2(CO)_8$ and 3.16g (40 mmol) of pyridine. The preparation of the catalyst complex and the hydroesterification of 1-decene was performed simultaneously by allowing the mixture to react at 80° C, under the carbon monoxide pressure of 10 atm. for 4 hours. When the autoclave was cooled and depressurized after the reaction, the complex of cobalt carbonyl with pyridine occurred in the form of a dark red viscous liquid separated from an upper phase consisting of reaction product and benzene. On standing for about 20 hours a small proportion of the catalyst complex dissolved in the reaction product further separated as a viscous liquid, and the amount of cobalt still dissolved in the reaction product was reduced to 0.13 mg. atom. Thus 99.4% of Co was recovered as a viscous liquid. The conversion of decene was 72%. The selectivity to linear ester and branched ester was 77% and 19%, respectively.

EXAMPLE 12

To a solution of 20 mmol of $Co_2(CO)_8$ in 50g of petroleum ether, 92 mmol of pyridine and 120 mmol of acetone were added, and the mixture was stirred. The reaction proceeded at normal room temperature and atmospheric pressure with evolution of carbon monoxide, and after 1 hour a dark red viscous liquid consisting of a complex of cobalt carbonyl with pyridine and acetone was obtained as a separate phase. The obtained liquid consisting of the catalyst complex was charged together with 0.3 mol of 1-decene and 0.2 mol of methanol in the same autoclave as used in Example 11 and the mixture was allowed to undergo reaction at 110° C, under the carbon monoxide pressure of 20 atm. for 3 hours. When the autoclave was cooled and depressurized after the reaction, the complex of cobalt carbonyl with pyridine and acetone again separated from the reaction product as a dark red viscous liquid. On standing for about 20 hours a small proportion of the catalyst complex dissolved in the reaction product further separated as a viscous liquid, and the amount of cobalt still dissolved in the reaction product was reduced to 0.08 mg. atom. Thus 99.8 percent of Co was recovered as a viscous liquid. The conversion of decene based on the amount of methanol used (0.2 mol) was 82%. The selectivity to linear ester and branched ester was 81% and 19%, respectively.

EXAMPLE 13

The same autoclave as used in Example 11 was charged with 0.2 mol of 1-decene, 0.2 mol of methanol, 20 mmol of $Co_2(CO)_8$, 80 mmol of pyridine, and 10 mmol of methylvinylketone. The preparation of the catalyst complex and the hydroesterification of 1-decene was performed simultaneously by allowing the mixture to react at 110° C, under the carbon monoxide pressure of 20 atm. for 6 hours. When the autoclave was cooled and depressurized after the reaction, the complex of cobalt carbonyl with pyridine and methylvinylketone occurred in the form of a dark red viscous liquid separated from an upper phase consisting of reaction product. On standing for about 20 hours a small proportion of the catalyst complex dissolved in the reaction product further separated as a viscous liquid, and the amount of cobalt still dissolved in the reaction product was reduced to 0.06 mg. atom. Thus 99.8 percent of Co was recovered as a viscous liquid. The conversion of decene was 64%. The selectivity to linear ester and branched ester was 81.5 and 18.5%, respectively.

EXAMPLE 14

The same autoclave as used in Example 11 was charged with 0.2 mol of 1-decene, 0.2 mol of methanol, 20 mmol of $Co_2(CO)_8$, 80 mmol of pyridine, and 20 mmol of mesityl oxide. The preparation of the catalyst complex and the hydroesterification of 1-decene was performed simultaneously by allowing the mixture to react at 90° C, under the pressure of carbon monoxide containing 5% of hydrogen, the pressure during the reaction period of 6 hours being kept constant at 20 atm. by continuously supplying carbon monoxide containing 5% of hydrogen. When the autoclave was cooled and depressurized after the reaction, the complex of cobalt carbonyl with pyridine and mesityl oxide occurred in the form of a dark red viscous liquid separated from an upper phase consisting of reaction product. On standing for about 20 hours a small proportion of the catalyst complex dissolved in the reaction product further separated as a viscous liquid, and the amount of cobalt still dissolved in the reaction product was reduced to 0.19 mg. Thus 99.5 percent of Co was recovered as a viscous liquid. The conversion of decene was 75%. The selectivity to linear ester and branched ester was 80.7 and 19.3%, respectively.

What is claimed is:

1. A process for the manufacture of a catalyst for use in hydroformylation and hydroesterification of olefins at low temperature and pressure, comprising the steps of:
   A. mixing cobalt carbonyl with at least one member selected from the group consisting of pyridine, alkylpyridine, formylalkylpyridine and vinylpyridine, and a hydrocarbon solvent at a weight ratio of $1 : (1 - 10) ; (4 - 30)$;
   B. compressing the mixture to $10 - 200$ kg/cm$^2$ of pressure of carbon monoxide and simultaneously heating the mixture to $80° - 200°$ C to produce a complex in the mixture;
   C. cooling the resultant reaction product to room temperature thereby producing a phase essentially comprising said hydrocarbon solvent and a phase essentially comprising said complex; and
   D. separating the phase essentially comprising the complex from the cooled reaction product.

2. The process of claim 1, wherein the cobalt carbonyl is $Co_2(CO)_8$.

3. The process of claim 1, wherein the vinylpyridine is one member selected from the group consisting of 2-vinylpyridine and 4-vinylpyridine.

4. The catalyst prepared by the method of claim 1.

5. A process for the manufacture of a catalyst for use in hydroesterification of olefins, comprising the steps of:
   A. mixing cobalt carbonyl with pyridine and one member selected from the group consisting of acetone, methylvinyl ketone and mesityl oxide at a molar ratio of $1 : (4 - 5); (1 - 10)$ in a hydrocarbon solvent;
   B. allowing the mixture to react at a temperature in the range of from normal room temperature to $110°$ C under a carbon monoxide pressure in the range of from 1 to 20 atm. to produce a complex in the mixture; C. cooling the resultant reaction product to room temperature thereby producing a phase essentially comprising said hydrocarbon solvent and a phase essentially comprising said complex; and
   D. separating the phase essentially comprising the complex from the cooled reaction product.

6. The process of claim 5, wherein the cobalt carbonyl is $Co_2(CO)_8$.

7. The catalyst prepared by the process of claim 5.

* * * * *